United States Patent
Schreiber et al.

(10) Patent No.: US 6,428,969 B1
(45) Date of Patent: Aug. 6, 2002

(54) METHOD FOR DETERMINING ONCOGENIC ACTIVITY OF A SUBSTANCE

(75) Inventors: Robert Schreiber, St. Louis, MO (US); Lloyd J. Old, New York, NY (US)

(73) Assignee: Ludwig Institute for Cancer Research, New York, NY (US)

(*) Notice: Subject to any disclaimer, the term of this patent is extended or adjusted under 35 U.S.C. 154(b) by 0 days.

(21) Appl. No.: 09/473,456

(22) Filed: Dec. 28, 1999

Related U.S. Application Data

(62) Division of application No. 08/938,295, filed on Sep. 26, 1997, now Pat. No. 6,063,359.

(51) Int. Cl.$^7$ .................. G01N 33/574; C12Q 1/68; C12Q 1/00; C12P 21/04; C12N 5/00

(52) U.S. Cl. .................. 435/7.23; 435/6; 435/4; 435/70.1; 435/325; 435/7.2; 435/7.21; 435/7.8; 435/7.1; 435/29; 435/34; 435/35; 536/23.1; 530/350

(58) Field of Search .................. 536/23.1; 435/325, 435/6, 69.5, 70.1, 7.23, 4, 7.2, 7.21, 7.8, 7.1, 29, 34, 35; 530/350

(56) References Cited

U.S. PATENT DOCUMENTS

| | | | |
|---|---|---|---|
| 4,736,866 A | 4/1988 | Leder et al. | |
| 5,087,571 A | 2/1992 | Leder et al. | |
| 5,174,986 A | 12/1992 | Berns | |
| 5,510,099 A | 4/1996 | Short et al. | |
| 5,602,300 A | 2/1997 | Gossen et al. | |

FOREIGN PATENT DOCUMENTS

| | | |
|---|---|---|
| WO | WO 89/05864 | 6/1989 |
| WO | WO 89/09272 | 10/1989 |

OTHER PUBLICATIONS

Ziai, 1985, Cancer Res., 45: 5877–5882.*
Kamijo et al, 1994, Science, 263: 1612–1615.*
Lu et al, 1994, Oncogene, 9: 1015–1019.*
Panelli et al, 1996, Cancer Immunol. Immunother., 42: 99–107.*
Timmerman et al, 1995, 43: 19–28.*
GC Sen, Cytokines in Health and Disease, "The Interferons," 2$^{nd}$ Ed., Chap. 14, pp. 199–208.*
Bach et al., The IFNγ Receptor: A Paradigm for Cytokine Receptor Signaling, *Annu. Rev. Immunol.* 15:563–91 (1997).
Broek et al., Decreased Tumor Surveillance in Perforin–deficient Mice, *J. Exp. Med.*, 184:1781–1790 (1996).
Dighe et al., Enhanced in Vivo Growth and Resistance to Rejection of Tumor Cells Expressing Dominant Negative IFNγ Receptors, *Immunity*, 1:147–456 (1994).
Dighe et al., Tissue–Specific Targeting of Cytokine Unresponsiveness in Transgenic Mice, *Immunity*, 3:657–666 (1995).
Donehower et al., Mice deficient for p53 are developmentally normal but susceptible to spontaneous tumors, *Nature*, 356:215–221 (1992).
Farrar et al., Identification of a functionally important sequence in the C terminus of the interferon–γ receptor, *Proc. Natl. Acad. Sci.*, 89:11706–11710 (1992).
Farrar et al., The Molecular Cell Biology of Interferon–γ and its Receptor, *Annu. Rev. Immunol*, 11:571–611 (1993).
Harvey et al., Spontaneous and carcinogen–induced tumorigenesis in p53–deficient mice, *Nature Genetics*, 5:225–229 (1993).
Huang et al., Immune Response in Mice That Lack the Interferon–γ Receptor, *Science*, 259:1742–1745 (1993).
Meraz et al., Targeted Disruption of the Stat1 Gene in Mice Reveals Unexpected Physiologic Specificity in the Jak–Stat Signaling Pathway, *Cell*, 84:431–442 (1996).
Rogers et al., Interleukin 1 participates in the development of anti–Listeria responses in normal and SCID mice, *Proc. Natl. Acad. Sci.*, 89:1011–1015 (1992).
Storer et al., Short–term carcinogenesis bioassay of genotoxic procarcinogens in PIM transgenic mice, *Carcinogenesis*, 16:285–293 (1995).
Tennant et al., Identifying Chemical Carcinogens and Assessing Potential Risk in Short–term Bioassays Using Transgenic Mouse Models, *Environmental Health Perspectives*, 103:942–950 (1995).
Yamamoto et al., Rapid induction of more malignant tumors by various geneotoxic carcinogens in transgenic mice harboring a human prototype c–Ha–ras gene that in control non–transgenic mice, *Carcinogenesis*, 17:2455–2461 (1996).
Gaspari et al., Impaired Interferon Production and Natural Killer Cell Activation in Patients with the Skin Cancer–prone Disorder, Xeroderma Pigmentosum, *J. of Clinical Invest.*, 92:1135–1142 (1993).
Farrar et al.., Identification of Two Regions within in the Cytoplasmic Domain of the Human Interferon–γ Receptor Required for Function, *The Journal of Biological Chemistry*, 266:19626–19635 (1991).
Venditti, J.M. (1981) In: Design of Models for Testing Cancer Therapeutic Agents, ed. I. Fidler and R. J. White, pp. 80–94. Van Nostrand Reinhold, New York.
Salomon, J. C. (1980) Cancer Induction by Methylcholanthrene and Metastatic Spread of Transplantable Tumor in Chediak Higashi (Beige) Mice. Cancer Immunol. Immunother., vol. 8(1): 67–70.

* cited by examiner

*Primary Examiner*—Scott D. Priebe
*Assistant Examiner*—Peter Paras, Jr.
(74) *Attorney, Agent, or Firm*—Fulbright & Jaworski LLP.

(57) ABSTRACT

A method for screening substances for oncogenic activity is disclosed. The method involves administering the substance to an animal lacking responsiveness to interferonγ and detecting a higher frequency or earlier time of tumor formation in the test animal compared to control animals. In addition, a method is provided for predicting the aggressiveness of a tumor in a patient.

18 Claims, 6 Drawing Sheets

METHOD FOR DETERMINING ONCOGENIC ACTIVITY OF A SUBSTANCE

This is a divisional of application Ser. No. 08/938,295; filed on Sep. 26, 1997, now U.S. Pat. No. 6,063,359.

REFERENCE TO GOVERNMENT GRANT

This invention was made with government support under Grant Number CA43059. The government has certain rights in the invention.

BACKGROUND OF THE INVENTION (1) Field of the Invention

This invention relates generally to the genesis and malignancy of tumors, and more particularly to methods for screening substances for oncogenic activity and to methods for assessing tumor aggressiveness.

(2) Description of the Related Art

Almost a century ago, Paul Erlich suggested that the immune system played a role in the elimination of spontaneously arising tumor cells (Ned. Tiijdschr. Geneeskd. 5(Pt. 1): 273, 1909, incorporated herein by reference). In 1970, Burnet coined the term "immune surveillance" to embody this concept and proposed that T cells would function as the major effectors in this system (Progr. Exp. Tumor Res. 13:1, 1970, incorporated herein by reference).

Recently, insight into the nature of the immune responses to tumors that were not nascently formed was provided by a study which suggested that the cytokine interferonγ (IFNγ) plays an important role in promoting tumor cell recognition and elimination (Dighe et al., Immunity 1:447–456, 1994, which is incorporated herein by reference). In this study, tumor cells derived from two methylcholanthrene-induced murine sarcomas in genetically different mice were transfected with a plasmid encoding a cytoplasmically truncated form of the murine IFNγ-receptor ligand binding chain (α chain). These cell lines are completely unresponsive to IFNγ due to overexpression of the functionally inactive IFNγ-receptor α chain at the cell surface. When these IFNγ-insensitive tumor cells were inoculated subcutaneously at low amounts (1 to $2 \times 10^4$ cells/mouse) into normal syngeneic mice, they formed rapidly progressing tumors in at least 80% of the injected mice. In contrast, mice inoculated with the same amount of IFNγ sensitive wild type tumor cells did not develop tumors. Dighe et al concluded that the development of host responses to the tumor studied requires the production of IFNγ by host cells, the capacity of the tumor to respond to IFNγ, and the development of specific T cell immunity.

Although this study identified a role for IFNγ in promoting rejection of transplantable tumors, they did not address the critical question of whether IFNγ participates in promoting host responses to nascently forming transformed cells, i.e., whether it is involved in promoting tumor surveillance. More importantly, the study did not address whether IFNγ responsiveness of the host cell played a role in tumor surveillance, which would be of critical importance in the development of an oncogenic screening method.

In another study of the physiological role of IFNγ in the immune response, knockout mice with an inactivated gene for the IFNγ receptor α chain were made and shown to be viable with no apparent phenotypic anomalies by 12 months (Huang et al., Science 259:1742–1745, 1993, incorporated herein by reference). The immune system in these IFNγR$^{-/-}$ mice appeared to develop normally in that no differences in the major lymphocyte subpopulations between mutant and wild-type mice were observed. However, the mutant mice had increased susceptibility to infection by Listeria monocytogenes and vaccinia virus despite normal cytotoxic and T helper cell responses. In addition, while the IFNγ-unresponsive mice generated a normal antigen-specific IgM and IgG1 response, they failed to develop a normal IgG2a response as indicated by decreased titers of antigen-specific IgG2a antibodies at twelve days after immunization with antigen.

Increased susceptibility to infection by microbial pathogens and viruses was also observed in knockout mice deficient in STAT1, an IFN-specific cytosolic transcription factor in the JAK-STAT signaling pathway (Meraz, et al., Cell 84:431–442, 1996, incorporated herein by reference). While these STAT1-deficient mice showed no overt developmental abnormalities and had normal populations and subpopulations of T cells, B cells, and macrophages, they died after infection with doses of Listeria monocytogenes and VSV that are sublethal in normal mice. Cells derived from the mutant mice were not responsive to IFNα and IFNγ but did respond normally to other cytokine ligands, including growth hormone, epidermal growth factor, and interleukin-10.

A recent study examined the susceptibility of perforin-deficient (PKO) mice to tumor induction by a sarcoma-inducing carcinogen, methylcholanthrene (MCA), a papilloma-inducing carcinogen, 7,12-dimethylbenzanthracene (DBMA) plus 12-O-tetradecanoylphorbol-13-acetate (TPA) (DBMA+TPA), and a sarcoma-inducing virus, Moloney murine sarcoma virus (MoMSV) (van den Broek et al., J. Exp. Med., 184:1781–1790, 1996). PKO mice subcutaneously injected with MCA developed sarcomas at the injection site at a higher frequency and with accelerated onset of tumor than observed in normal MCA-treated mice. In addition, although PKO and normal mice injected intramuscularly with MoMSV displayed similar numbers and kinetics of tumor onset, MoMSV-induced tumors were larger and regression was retarded in the PKO mice than in normal mice. However, the incidence and kinetics of DMBA+TPA-induced papillomas were similar in PKO and normal mice. The authors concluded that several mechanisms probably control tumor growth, with perforin-mediated cytotoxicity playing a role in some types of tumors, but not in others.

Assessing the carcinogenic potential of chemical compounds is indispensable in drug development and in identifying environmental carcinogens. Currently, the gold standard carcinogenicity test is the rodent bioassay performed by the National Toxicology Program (NTP) at Research Triangle Park, N.C. (Ashby et al., Mutat. Res., 257: 229–306, 1991, incorporated herein by reference). The NTP rodent bioassay lasts more than two years, requires a large number of experimental animals, a large amount of laboratory space for animal testing, and a large number of laboratory technicians. The cost of the NTP bioassay is so high that only a few chemicals per year can be evaluated. However, there are many chemicals in commercial use or in the environment that have not been tested, and thousands of new chemicals are synthesized every year. Thus, there is much interest in developing improved animal bioassays that can evaluate the oncogenic potential of chemical compounds within a relatively short period of time.

Recently, in a brief reference to unpublished observations, Bach et al. (Annu. Rev. Immunol. 15:563–591, 1997, incorporated herein by reference) stated that the chemical carcinogen 3-Methylcolanthrene produced more tumors in α chain knockout mice than in wild-type controls. This reference discussed the role of IFNγ in host surveillance. Nevertheless, the authors did not provide any suggestion as to whether the knockout mice or wild-type controls could be used in a carcinogenicity screening model nor did they provide sufficient details of their findings to allow one to assess the possibility of such use.

Genetically modified mice that carry specific oncogenes or inactivated tumor-suppressor genes have been proposed as candidate animal models for rapid carcinogenicity testing. (See, e.g., Tennant et al., *Envir. Health Perspect.* 103:942–950, 1995; Yamamoto et al., *Carcinogenesis* 17:2455–2461, 1996; and Berns, U.S. Pat. No. 5,174,986, each of which is incorporated herein by reference). Mutant mice that reportedly respond more rapidly and at higher frequency to various carcinogens than wild-type mice include v-Ha-ras transgenic mice (Tennant et al., supra), c-Ha-ras transgenic mice (Yamamoto et al., supra), transgenic mice that overexpress the pim-1 oncogene in lymphoid tissues (Storer et al., *Carcinogenesis* 16:285–293, 1995, incorporated herein by reference and Berns, supra), and p53 heterozygous knockout mice (Tennant et al., supra).

These known animal models have characteristics that may limit their use in a carcinogenic screening assay. For example, the $p^{53-/+}$ mice apparently respond differently to different classes of carcinogens in that tumors were induced by the mutagenic carcinogens p-cresidine and 4-vinyl-1-cyclohexene diepoxide (VCD), but not by the nonmutagenic carcinogens N-methylolacrylamide (NMOA) and reserpine (Tennant et al., supra). In addition, transgenic mice that express an oncogene in only one tissue may not be able to detect the broadest range of tissue specific carcinogenic activity. Indeed, it was recently suggested that data showing a very weak lymphoma response by pim-1 mice to three genotoxic carcinogens that do not normally induce lymphomas and a negative response to a known mouse lymphomagen raised concern that pim-1 mice are not sufficiently sensitive to established carcinogens to justify their routine use in a short-term carcinogenic screening assay (Storer et al, supra). Finally, data obtained with transgenic mice having inappropriate expression of an oncogene may not be predictive of the effect of such compounds in animals with normal expression of the oncogene. Therefore, it would be desirable to develop a screening assay that uses an animal model in which tumors are rapidly induced by a wide variety of mutagenic and nonmutagenic carcinogens that act on different target tissues and through different mechanisms.

SUMMARY OF THE INVENTION

Briefly, therefore, the present invention is directed to a method for rapid in vivo screening of substances for carcinogenic activity and, in addition, a new method for diagnosing the clinical aggressiveness of tumors. Accordingly, the inventors herein have succeeded in discovering that IFNγ-insensitive mice are surprisingly much more susceptible to chemically induced tumor formation than IFNγ-sensitive, parental mice. Moreover, it has been discovered that a significant number of tumor cell lines are unresponsive or show reduced responsiveness to IFNγ.

One aspect of the present invention, therefore, provides a method to determine the oncogenic potential of a substance of interest, which comprises administering the substance to at least one IFNγ-insensitive test animal and monitoring the test animal for tumor formation. Tumors occurring at a higher frequency or at an earlier time in the IFNγ-insensitive test animal than spontaneously arising tumors in an untreated IFNγ-insensitive animal indicates the substance is oncogenic. Reference to an untreated animal is intended to mean a control animal not receiving administration of the test substance or an animal being evaluated during a period in which the test substance has not been administered although the test substance could be given either before or after the period of no treatment. The untreated animal can receive administration of a carrier vehicle in which the drug would have been administered or, alternatively, the untreated animal can receive no administration at all.

The method also embraces administering a known dose of the substance to each member of a group of IFNγ insensitive test animals and comparing the rate and/or frequency of tumors in the test group with that for tumors arising in a control group of IFNγ-insensitive animals treated with a known, oncogenic amount of a known carcinogen, thus providing an indication of the oncogenic potential of a test compound relative to that of the known carcinogen.

In another aspect of the invention, a method for predicting tumor aggressiveness is provided. The method comprises testing a tumor sample from a patient for sensitivity to IFNγ. Insensitivity to IFNγ would indicate that the tumor is less likely to be recognized by the patient's immune system and is thus likely have an extremely aggressive clinical course.

Among the several advantages found to be achieved by the present invention, therefore, may be noted the provision of a new in vivo approach for testing the oncogenicity or carcinogenicity of substances in which the method is inexpensive and simple to perform, requiring only a relatively short testing period compared to currently available methods; and the provision of methods for predicting the aggressiveness of a tumor in a patient.

DESCRIPTION OF THE PREFERRED EMBODIMENTS

Figure 1A:
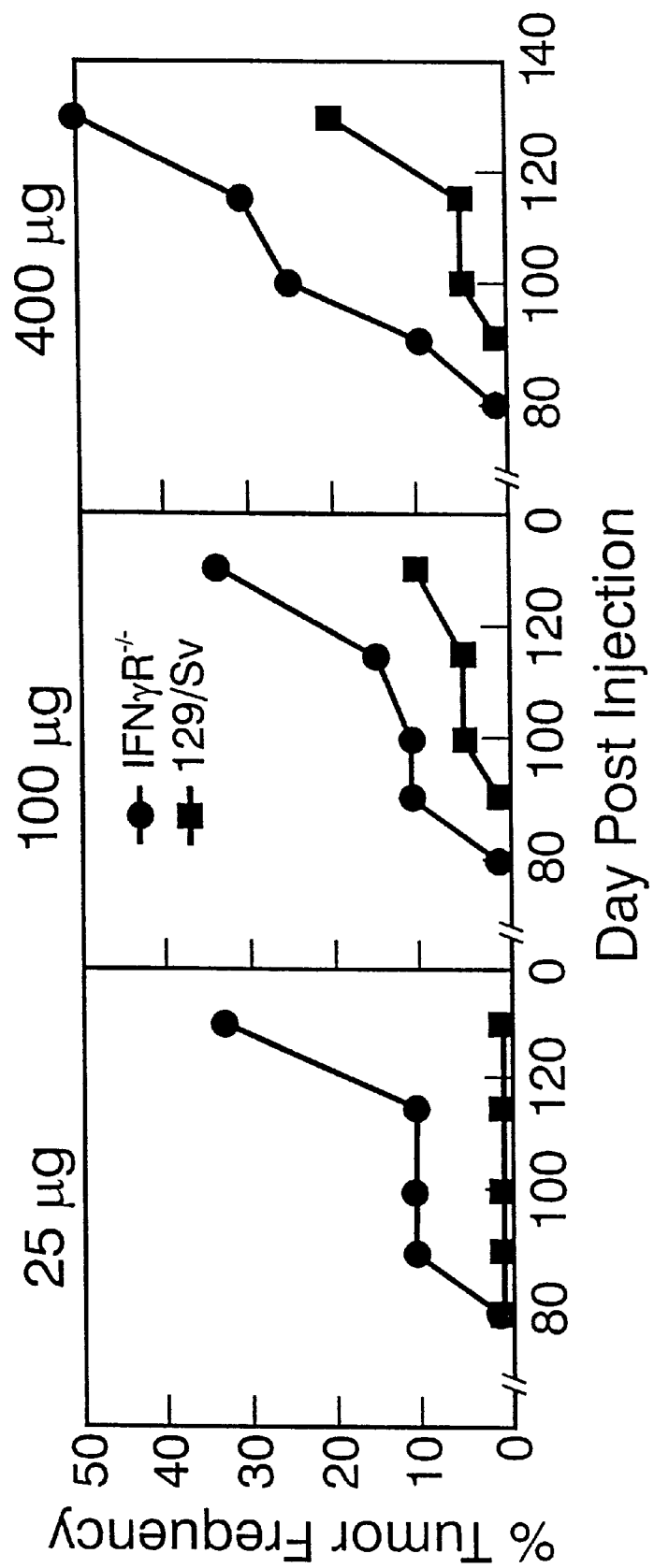
FIGS. 1(A–C) illustrates the increased susceptibility of IFNγ-insensitive mice to chemically induced and spontaneous tumor formation showing (A) the percentage of groups of 15–20 IFNγR$^{-/-}$ and 129/sv (wild type) mice with a tumor over 5 mm in diameter represented as a function of the number of days after subcutaneous injection with a single dose of 25, 100, or 400 μg of the chemical carcinogen 3-methylcholanthrene (MCA); (B) the percentage of groups of 20–25 IFNγR$^{-/-}$, Stat1$^{-/-}$ and 129/sv mice that developed a tumor over 5 mm within 130 days after subcutaneous injection with a single dose of 1.5, 6.25, 25, 100, or 400 μg MCA; and (C) the percentage of IFNγR-$^{-/-}$×p53$^{-/-}$ double knockout mice and 129/sv×p53$^{-/-}$ single knockout mice that were tumor free as a function of time post birth.

The present invention is based upon two surprising and unexpected discoveries: (1) that immune recognition and development of an anti-tumor response against a nascently formed tumor cell requires that the tumor cell be sensitive to IFNγ and (2) that a significant number of certain human tumors are unresponsive to IFNγ. Because nascently formed tumor cells must be IFNγ-sensitive for immune rejection, animals whose cells lack responsiveness to IFNγ are highly susceptible to chemically induced tumor formation. In addition, it is believed that tumor cells that have become insensitive to IFNγ will have a more aggressive clinical course than IFNγ-sensitive tumor cells.

One aspect of the invention is a method for determining the oncogenicity of a substance, which comprises administering the substance to an IFNγ-insensitive animal and detecting tumor formation in the animal. The IFNγ-insensitive animal is a non-human animal, which can include but is not limited to mice, rats, rabbits, guinea pigs, non-human primates, and the like. Preferably, the method is carried out with IFNγ-insensitive mice. The phenotype of the IFNγ-insensitive animal can be produced by a defect, i.e. a biochemical lesion, in the IFNγ-signaling pathway including a defect in the IFNγ ligand itself. Animals having such a biochemical lesion lack a functional gene product that is essential for an effective IFNγ-signaling pathway or lack a functional IFNγ. This pathway, which is one of the most understood cytokine signaling pathways, includes the following IFNγ-signaling proteins: IFNγ, IFNγ-receptor α subunit, IFNγ receptor β subunit, Jak1, Jak2 and Stat1. (see, for example, Bach et al., *Annu. Rev. Immunol.* 15: 563, 1997, which is incorporated herein by reference.) Any one or more of these IFNγ-signaling proteins can be functionally absent such that IFNγ signaling does not occur or is diminished in magnitude.

The biochemical lesion can be caused by any naturally occurring or man-made mutation in a gene coding for an IFNγ-signaling protein that either inactivates expression of the protein or results in expression of a biologically inactive form of the signaling protein. Alternatively, the lesion can be due to the introduction of a gene that overexpresses a biologically inactive form of the IFNγ-signaling protein that effectively blocks biological function of the normal signaling protein. Expression of such a dominant-negative IFNγ-signaling protein mutant may be specific to a single tissue in the mutant animal, thereby providing tissue-specific IFNγ unresponsiveness. Preferably, all cells comprising the mutant animal express the dominant-negative mutant and are unresponsive to IFNγ.

The genes coding for the members of the IFNγ-signaling pathway have been cloned and characterized in mice and may be readily obtained for other non-human animals. (see, for example, Bach et al., supra, and references cited therein). Thus, one skilled in the art, using well-known techniques, can readily inactivate one of these genes or introduce therein a missense or nonsense mutation that results in a biologically inactive protein. For example, the target IFNγ-signaling gene may be inactivated by homologous recombination techniques such as those described in Huang et al, supra and Meraz et al., supra. In brief, embryonic stem cells are transfected with a replacement vector that contains part of the target gene disrupted by a neomycin resistance gene fused to the herpes simplex virus thymidine kinase gene for negative selection against nonhomologous recombination events. Embryonic stem cell clones with homologous insertion of the replacement vector are identified by PCR and/or Southern blot analysis and positive clones are used to produce male chimeras which are then mated with females having the desired genetic background. The heterozygote offspring are interbred to generate mutant animals heterozygous or homozygous for the disrupted IFNγ-signaling gene as detected by PCR and/or Southern blot analysis.

Transgenic animals with tissue-specific IFNγ unresponsiveness may be generated by placing a CDNA encoding a dominant-negative IFNγ-signaling protein mutant under the control of a promoter specific for that tissue and transfecting the promoter-cDNA construct into embryonic stem cells using standard techniques. For example, transgenic mice have been generated that express an IFNγ-receptor α chain mutant under the control of either the human lysozyme promoter or the murine ick proximal promoter and thus display tissue-specific unresponsiveness in the macrophage or T cell compartments, respectively. (Dighe et al., *Immunity* 3:657–666, 1995, incorporated herein by reference.)

The IFNγ-insensitive animal can also carry one or more other mutations that render the animal more susceptible to tumor formation. Such mutations include but are not limited to the inactivation of a tumor suppressor gene or the overexpression of an oncogene. Such animals can be readily prepared using standard techniques. For example, gene targeting methods have been used to generate mice that are heterozygote or homozygote for a germ-line mutation in the tumor suppressor gene p53 (Donehower et al., *Nature* 356:215–221, 1992, incorporated herein by reference).

It is believed that animals that are heterozygous for a germ-line mutation in the tumor supressor gene, p53, develop a wider range of tumors than animals that are homozygous. Thus, it is preferred that the IFNγ-insensitive animals having combined defects for use in the present invention, be heterozygous for a p53-gene defect in addition to being either homozygous for a IFNγ-receptor defect (p53$^{+/-}$×IFNγR$^{-/-}$) or a Stat1 defect (p53$^{+/-}$×Stat1$^{-/-}$).

The oncogenic potential of any substance can be tested by the method of the invention. By oncogenic potential or oncogenicity of a substance, it is meant that the substance is capable of generating a malignant tumor or neoplasm in an individual exposed to the substance. The terms oncogenic and oncogenicity are used herein interchangeably with the terms carcinogenic and carcinogenicity, respectively.

As used herein, the term "substance" includes but is not limited to inorganic or organic chemical compounds as well as chemical elements. Also included are biochemical molecules such as nucleic acids, proteins, lipids, lipoproteins, and carbohydrates. Because viruses are sometimes associated with the induction of tumors, viruses are also included within the term "substances" as are microorganisms such as bacteria, fungi, and the like. The substance to be tested can be a sample of substantially inorganic origin such as a water or air sample containing certain contaminants or a sample of biological origin which occurs in nature or which has been modified and which may be consumed by or in some manner brought into contact with humans. The substance tested can also include mixtures of known and/or unknown chemicals. For example, known chemical carcinogens have been compiled in a number of reference publications such as in the CRC Handbook of Chemistry and Physics, 75th Ed., Lide and Frederikse Eds., CRC Press, Boca Raton, 1994, pp. 16–34 to 16–37 which is incorporated by reference. In general, the method of the invention may be used to assess the oncogenic potential of any substance that does not cause the death of the IFNγ-insensitive animal before the onset of a tumor. For example, it would likely be impractical to test the oncogenic potential of poisons such as cyanide.

The substance can be administered to the IFNγ-insensitive animal by any method normally used in animal bioassays, including, but not limited to, topically to the skin, subcutaneous injection, intraperitoneal injection, intramuscular injection, orally in the diet or by intubation, and inhalation. Preferably, the substance is administered by subcutaneous injection.

The substance to be tested is generally administered in a formulation that is adapted for the chemical nature of the substance, the desired target organs(s), and the route of administration. The formulation can include a vehicle or carrier liquid which can be aqueous based such as a saline solution or solution containing physiological concentrations of other non-toxic salts, five percent aqueous glucose solution, sterile water or the like. Alternatively, the vehicle can be a non-aqueous liquid such as polyethylene glycol, propylene glycol, peanut oil or corn oil or the like. Such formulations are well known in the art (for example, see *Remington's Pharmaceutical Sciences*, Ed. Arthur Osol, 16th ed., 1980, Mack Publishing Co., Easton, Pa.). By way of example only, the method can involve dissolving an organic compound to be tested for fibrosarcoma induction in corn oil and subcutaneously injected into the IFNγ-insensitive animal. If the papilloma-inducing ability of the compound is to be tested, the compound can be applied to the animal's skin in acetone or a similar vehicle. A substance's ability to induce stomach or liver tumors may be assessed by putting the substance in the animal's food or drinking water. Also, substances such as biochemical molecules or viruses can be injected into the test animal in a physiological saline solution, sterile water, or other suitable aqueous solutions in which the substance is structurally and/or functionally stable, such as buffered solutions.

A known amount of the substance can be administered to the test animal. The test animal can receive a single dose or multiple doses of the test substance. The specific dose is calculated according to the approximate body weight or body surface area of the IFNγ-insensitive animal, or the volume of body space to be occupied. Calculation of the dose will also be dependent upon the chemical nature of the substance and the particular administration route selected. Such calculations can be made without undue experimentation by one skilled in the art.

Following administration of the substance of interest, the IFNγ-insensitive animal is then monitored for tumor development. It is desirable that the monitoring period be sufficiently long to allow chemically-induced tumor development but not so long that spontaneous tumor development appears. Preferably the monitoring period is from about three weeks to about a year, more preferably from about six weeks to about 30 weeks, and even more preferably from about eight weeks to about 20 weeks. During the monitoring period, the IFNγ-insensitive animal is preferably examined on a regular basis such as once or twice each week, or once every two weeks.

The terms tumor development or tumor formation are intended to refer to the appearance of a tumor in an animal in a manner in which the tumor can be detected. Tumors can be detected by any suitable method known in the art such as by visual inspection of the site of topical administration or subcutaneous injection, by palpation, by biopsy, and/or by autopsy. Any tumor detected can be analyzed by methods known in the art such as by histological or histochemical examination of the tumor. When monitoring for tumors detectable only by autopsy, it is preferred that multiple, genetically identical animals receive the same dose of the chemical compound by the same administration route followed by sacrifice at varying intervals to provide for the earliest detection of tumor onset.

The frequency of tumor formation can be measured as the number of tumors observed per animal or per group of animals. Alternatively, the number of animals developing tumors can be determined. Assessment of the number of tumors or animals having tumors can be performed during the course of monitoring or on a given day such as at the end of the monitoring period.

The oncogenicity of a substance is preferably tested by administering the substance in a suitable vehicle comprising a solvent or carrier to a group of IFNγ-insensitive animals and comparing the frequency and/or time of tumor onset to that for spontaneous tumor development in a group of IFNγ-insensitive control animals treated with the vehicle alone or receiving no treatment with the test substance or vehicle. In addition, a dose response study can be performed by administering varying doses of the substance to separate test groups of IFNγ-insensitive animals.

Although one animal can be tested with a given substance or dose of that substance, generally, it is preferred that a group of at least about three IFNγ-insensitive animals be tested. Under other circumstances such as where greater sensitivity or reduced variability is desired, larger groups can be tested comprising from about 4 to about 25 animals or more, in particular, 4 to 5 animals, 9 to 10 animals or 20 to 25 animals. In general, it is believed that a group of at least about 15 to 20 animals is most preferred in the method of assessing oncogenicity of the present invention. It is also preferred that the test and control groups consist of genetically identical IFNγ-insensitive animals of similar age and weight.

A genetically identical animal as used herein is intended to mean that the animals are deficient in the same IFNγ-signaling protein and otherwise have the same pure genetic background.

IFNγ-insensitive mice derived on a pure 129/Sv/Ev genetic background are the preferred animals for use in the invention. The test and control groups can be comprised of animals having the same sex or can include equal numbers of male and female animals, depending on the target tissue (s).

The degree of oncogenicity of the substance relative to the oncogenicity of a known carcinogen can be determined by comparing the time and/or frequency of tumor onset in IFNγ-sensitive animals receiving approximately equal doses of the substance of interest and the reference carcinogen, respectively. Alternatively, varying dosages of the substance of interest can be administered to separate groups of test IFNγ-insensitive animals until the average latency period between treatment and tumor development is the same as that in control IFNγ-insensitive animals treated with a specified dose of the carcinogen. The carcinogen can be a compound known to be oncogenic in mammals or identified as having carcinogenic potential by the NTP rodent bioassay.

The discovery of an IFNγ-dependent tumor surveillance system and the identification of IFNγ-insensitive tumor cell lines provide the basis for another aspect of the invention, which is a method to predict the clinical aggressiveness of a tumor in a patient. By clinical aggressiveness of a tumor reference is made to the ability of the tumor to expand and invade adjacent or distant tissue sites. The method for assessing tumor aggressiveness comprises testing a tumor sample from a patient for sensitivity to IFNγ. Insensitivity to IFNγ would indicate that the tumor is less likely to be recognized by the patient's immune system and will thus likely have an extremely aggressive clinical course. The method is applicable to human patients as well as to veterinary patients.

Responsiveness to IFNγ may be tested by treating the tumor sample with IFNγ and assaying for induction of one or more of the effects of IFNγ (Farrar et al., *Annu. Rev. Immunol.* 11:571–611, 1993 and incorporated herein by reference.) For example, enhanced MHC protein expression on the surface of cells indicates responsiveness to IFNγ and may be detected by flow cytometry using anti-H-2 Kd monoclonal antibody (class I) or an anti-class II antibody (Farrar et al., *J. Biol. Chem.* 266:19626–19635, 1991, incorporated herein by reference). In addition, the ability of IFNγ to induce nitric oxide production in tumor cells in the presence of lipopolysaccharide can be examined as described elsewhere (Farrar et al., *Proc. Natl. Acad. Aci. USA* 89:11706–11710, 1992, incorporated herein by reference). Antiproliferative and antimetabolic activities of IFNγ on tumor cells can be assessed by thymidine incorporation (Rogers et al., *Proc. Natl. Acad. Sci. USA* 89:1011–1015, 1992, incorporated herein by reference) and by 3-[4,5-dimethyl-thiazol-2-yl]-2,5-diphenyltetrazolium bromide assays (Green et al., *J. Immunol. Meth.* 70:257–262, 1984, incorporated herein by reference). Responsiveness to IFNγ can also be tested by quantitating levels of mRNA expressed by genes known to be induced by IFNγ, including interferon regulatory factor 1 (IRF1), guanylate-binding protein (GBP1), MHC class II transactivating protein (CIITA), the complement protein C3, and the complement protein factor B.

In circumstances in which a positive control is desired, the effect of IFNγ on the tumor sample can be compared with the effect of IFNγ on non-tumor cells from the patient, preferably of the same tissue type as the tumor sample.

Preferred embodiments of the invention are described in the following examples. Other embodiments within the scope of the claims will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the preparation of IFNγ-receptor α chain knockout mice (IFNγR$^{-/-}$) by gene targeting as described previously (Huang et al, supra).

The murine IFNγ cDNA (Hemmi et al., PNAS 86:9901–9905, 1989, incorporated herein by reference) was used as a probe to isolate partially overlapping 15 and 17.5 kb fragments that encompassed the entire IFNγR gene (approximately 25 kb) from an EMBL3 genomic library of brain DNA from C57B1/6 mice. The replacement vector encompassed 10 kb of the gene and contained exons V to VII, with exon VI encoding the transmembrane portion of the receptor. The gene was disrupted by inserting a blunted XhoI-SalI fragment of pMC1neopA (Stratagene, LaJolla, Calif.), which encodes the neomycin resistance gene, into the blunted Aat II site of exon V. Embryonic stem (ES) cells were transfected with this vector. ES clones containing homologous insertion of the replacement vector were identified by screening the lysates of G418-resistant colonies for a 0.8-kb fragment generated by the polymerase chain reaction (PCR) using one primer derived from a genomic wild-type sequence immediately 5' of the targeting construct and a second primer derived from the thymidine kinase promoter of the neomycin resistance gene. Homologous recombination in PCR identified clones was verified by Southern blot analysis of Bam HI-digested genomic DNA using as a probe a 2.0-kb exon V-containing HindIII fragment, which would detect a 4.7 kb Bam HI fragment if homologous insertion had disrupted exon V.

Chimeric founder males were mated with 129/Ev/Sv females to yield heterozygous (129/Sv/Ev×129/Sv/Ev)F$_1$ offspring. Interbreeding of these offspring produced wild-type and IFNγR$^{-/-}$ (129/Sv/Ev×129/Sv/Ev)F$_2$ offspring. The protein encoded by the disrupted IFNγ gene in the IFNγR$^{-/-}$ mice is not functional because it lacks the cytoplasmic domain needed for signaling and because the disruption site is upstream of a cysteine residue that is essential for ligand binding.

EXAMPLE 2

This example illustrates the preparation of Stat1-deficient mice using gene targeting as previously described (Meraz et al., supra).

Genomic clones containing overlapping portions of the murine Stat1 gene were isolated from a λFix II murine 129/Sv genomic library (Stratagene, LaJolla, Calif.) using the full-length human Stat1 cDNA as a probe. A Stat1 targeting construct was designed to replace the first three translated exons of the Stat1 gene and 0.7 kb of upstream sequence with a neomycin resistance cassette and to insert the herpes simplex virus thymidine kinase gene 8.0 kb downstream for negative selection against nonhomologous recombination events. This targeting construct was generated by inserting an 8 kb BamH1-SauI fragment of a clone containing exon 4 immediately upstream of the polyoma enhancer promoter-driven herpes simplex virus thymidine kinase gene in the targeting vector pTK.NEO.UMS (Reis et al., *EMBO J.* 13: 4798–4806, 1994). The 5. end of the targeting construct was constructed by inserting a 900 bp NotI-SauI fragment of a Stat1 genomic clone that contained an intronic sequence just upstream from the ATG start codon in exon 1.

The targeting vector was electroporated into the GS-1 embryonic stem (ES) cell line and transfectants were positively and negatively selected using G418 and FIAU, respectively, as described by Muller et al., *Science* 264:1918–1921, 1994, which is incorporated herein by reference. Homologous recombination in resistant clones was identified by southern blot analysis of BamHI-digested genomic DNA using a 0.7 kb probe derived from a region of the Stat1 gene that was 0.9 kb upstream from the targeted site. This probe hybridized with 8.5 kb BamHI and 5.5 kb fragments from the wild-type and disrupted alleles, respectively.

Three recombinant ES clones containing a disrupted Stat1 allele were microinjected into blastocysts to produce male chimeras that were then bred to C57BL/6 or 129/Sv females. Heterozygote by heterozygote breedings of the F$_1$ offspring produced F$_2$ offspring that segregated in a Mendelian distribution into groups of Stat1$^{+/+}$, Stat1$^{+/-}$, and Stat1$^{-/-}$ mice.

EXAMPLE 3

This example illustrates the generation of IFNγR$^{-/-}$× p53$^{-/-}$ double knock out mice.

Mice homozygous for a disrupted p53 gene were generated essentially as described by Donehower et al., supra. In brief, the p53 gene was disrupted by electroporating ES cells with a p53 targeting vector containing 3.7 kb of the genomic p53 gene interrupted in exon 5 by a PolII-neo expression cassette (Soriano et al., *Cell* 64:693–702, 1991) that was missing a polyadenylation signal. The targeting vector also contained a 450 bp deletion of the p53 gene which contained 105 bp of exon 5 and about 350 bp of intron 4. A G418, FIAU-resistant clone with a disrupted p53 allele was used to generate germ-line chimeric male mice which were bred to 129/Sv/Ev females to produce p53$^{+/-}$×129/Sv/Ev offspring. These offspring were interbred to produce p53$^{-/-}$×129/Sv/Ev mice which were bred to IFNγR$^{-/-}$×129/Sv/Ev mice from Example 1 to produce IFNγR$^{-/-}$×p53$^{-/-}$ mice on a 129/Sv/Ev background.

EXAMPLE 4

This example illustrates that IFNγR$^{-/-}$ mice are more susceptible than wild-type mice to chemically induced tumor formation.

Initially, tumor formation was examined in groups of 15–20 IFNγR$^{-/-}$ mice generated as described in Example 1 and wild type inbred 129/Sv/Ev mice as controls. All animals were greater than 6 weeks old (ranging in age from about 6 to about 12 weeks). The 129/Sv/Ev background was specifically chosen for these experiments since 129/Sv/Ev mice are relatively resistant to the tumorigenic actions of MCA and the pure background of the mice insured that in vivo growth of the resulting tumors could be studied using tumor transplantation approaches. The knockout and control mice were injected subcutaneously in a single dose with 25, 100, or 400 μg of the chemical carcinogen 3-methylcholanthrene (MCA) diluted in peanut oil and monitored for tumor development at the injection site for a period of 130 days. The results are shown in FIG. 1A, which represents the percentage of mice in each group with a tumor over 5 mm as a function of the number of days after injection.

Tumors were detected in IFNγR$^{-/-}$ mice at 90 days in all dose groups. The IFNγR$^{-/-}$ mice developed tumors more frequently and at earlier times than the wild-type mice at all doses examined. At 130 days, the end of the observation period, 50% of the IFNγR$^{-/-}$ mice treated with 400 μg MCA developed tumors, while tumors were detected in only 20% of the wild-type mice. In addition, the mutant and wild-type mice showed different sensitivities to MCA treatment. Whereas wild-type mice formed tumors only when treated with MCA doses of 100 μg or higher, a high percentage of IFNγR$^{-/-}$ mice still formed tumors even at the lower MCA dose of 25 μg. This latter observation was particularly striking since it established an absolute difference in MCA sensitivity between IFNγ responsive and unresponsive mice.

EXAMPLE 5

This example illustrates that two different types of IFNγ-insensitive mice are more susceptible to chemically-induced tumors than wild-type mice.

Figure 1B:
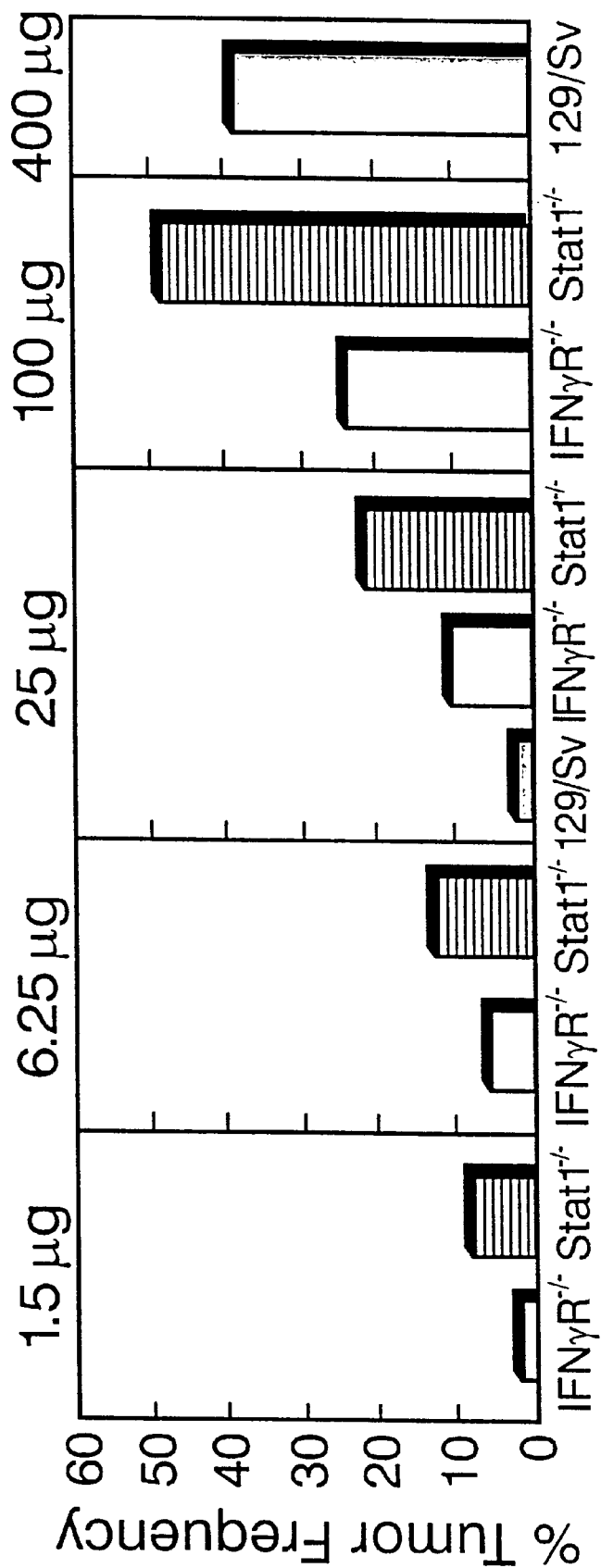

Groups of IFNγR$^{-/-}$ mice and STAT1$^{-/-}$ mice were generated as described in Examples 1 and 2 and compared to a control group of 129/Sv/Ev wild-type mice. All animals were greater than 6 weeks old (ranging in age from about 6 to about 12 weeks). Each of 20–25 animals per group, were injected subcutaneously with a single dose of MCA at 1.5, 6.25, 25, 100 or 400 μg and monitored for tumor development. FIG. 1B shows the percentage of mice that developed an injection-site tumor over 5 mm in diameter within 130 days after MCA injection for each group.

Both types of IFNγ insensitive mice developed MCA-induced tumors more frequently than wild-type mice. Tumor formation was detected in IFNγR$^{-/-}$ mice treated with as little as 6.25 μg MCA. Even greater MCA-induced tumor formation was observed in the Stat1 knock out mice. At every dose examined, Stat1$^{-/-}$ mice developed tumors approximately two times more frequently than the IFNγR$^{-/-}$ mice and tumors could be detected even at the lowest dose of 1.6 μg MCA/mouse. In contrast, the wild-type mice developed tumors when challenged with 400 μg MCA, but not with 25 μg MCA. A histologic comparison of the tumors detected in IFNγ-responsive and IFNγ-unresponsive mice indicated that MCA induced histologically indistinguishable fibrosarcomas in the three mouse strains (data not shown). Thus, IFNγ plays a critical role in providing the host with a mechanism to eliminate chemically induced, nascently transformed cells.

EXAMPLE 6

This example illustrates that IFNγ is also involved in immune surveillance of spontaneously formed tumors.

IFNγ-sensitive and IFNγ-insensitive mice that were also deficient for the p53 tumor suppressor gene were used as models for spontaneous tumor development. These animals would be expected to have a greater propensity for the development of spontaneous tumors than IFNγ-sensitive or IFNγ-insensitive animals with an intact p53 tumor suppressor gene.

Figure 1C:
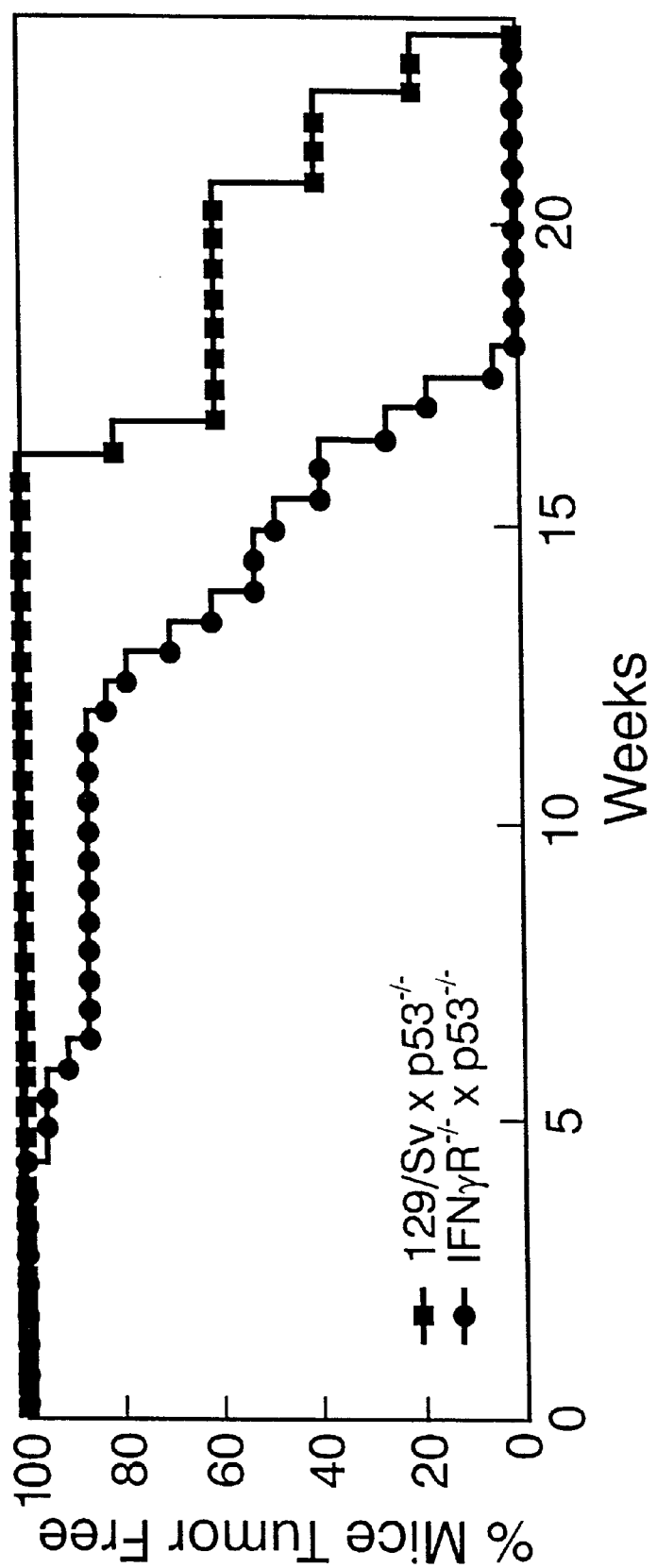

IFNγR$^{-/-}$×p53$^{-/-}$ and 129/Sv/Ev×p53$^{-/-}$ mice were generated as described in Example 3 and checked every 3–5 days for spontaneous tumor formation. Mice with obvious tumors or which appeared moribund were sacrificed and examined for tumor burden. The data, represented as the percentage of mice tumor free over time, is shown in FIG. 1C.

IFNγ-sensitive, p53 single knockout mice formed tumors with a mean time to tumor detection of 19.6 weeks, a result that is consistent with published data. (Donehower et al., supra; Jacks et al., *Curr. Biol.* 4:1, 1994; and Harvey, et al., *Nature Genetics* 5:225, 1993; each of which is incorporated herein by reference.) In contrast, IFNγR$^{-/-}$×p53$^{-/-}$ double knock out mice formed tumors significantly more rapidly with a mean time until tumor detection of 14.1 weeks ($p<0.01$ as determined by the Wilcoxan Rank Sum Test). The IFNγ-sensitive and IFNγ insensitive mice also displayed differences in the types of tumors that formed. Whereas all the tumors isolated from p53$^{-/-}$×129/Sv/Ev mice in this experiment were thymomas and lymphosarcomas, the p53$^{-/-}$×IFNγR$^{-/-}$ mice developed a wider range of tumors that also included several teratomas, two hemangiomas and a chondrosarcoma. Taken together, the results described herein demonstrate that IFNγ plays a central role in promoting tumor surveillance for both chemically induced and spontaneously forming tumors.

EXAMPLE 7

This example illustrates that IFNγ-insensitive tumors grow equally well in IFNγ-sensitive or IFNγ-insensitive mice.

Since IFNγR$^{-/-}$ and Stat1 deficient mice are unresponsive to IFNγ in all tissues, the experiments described above did not define whether increased tumor formation resulted from the lack of IFNγ responsiveness by tumor cells or by host immune cells. To distinguish between these two possibilities, tumor cell lines were derived from tumors formed in individual MCA treated IFNγR$^{-/-}$ mice. The tumors were surgically excised from the IFNγR−/− mice, passaged two times in SCID mice, followed by one passage in 129/Sv/Ev mice, and then maintained in culture in RPMI supplemented with 10% fetal calf serum, 1% glutamine, 1 mM sodium pyruvate, 50 units/ml penicillin, 10 mM non-essential amino acids, 50 μg/ml streptomycin and $5 \times 10^{-5}$ M β-mercaptoethanol. Seven of the resulting tumor cell lines (denoted RAD-gR.14, 21, 26, 27, 28, 30, and 43) were harvested with trypsin, washed two times with phosphate buffered saline and injected subcutaneously at a dose of $1 \times 10^6$ cells/mouse into syngeneic wild type and IFNγR−/− mice. The seven RAD-gR tumor cell lines were found to grow equally well in either naive IFNγ-sensitive or IFNγ-insensitive mice (data not shown).

Figure 2:
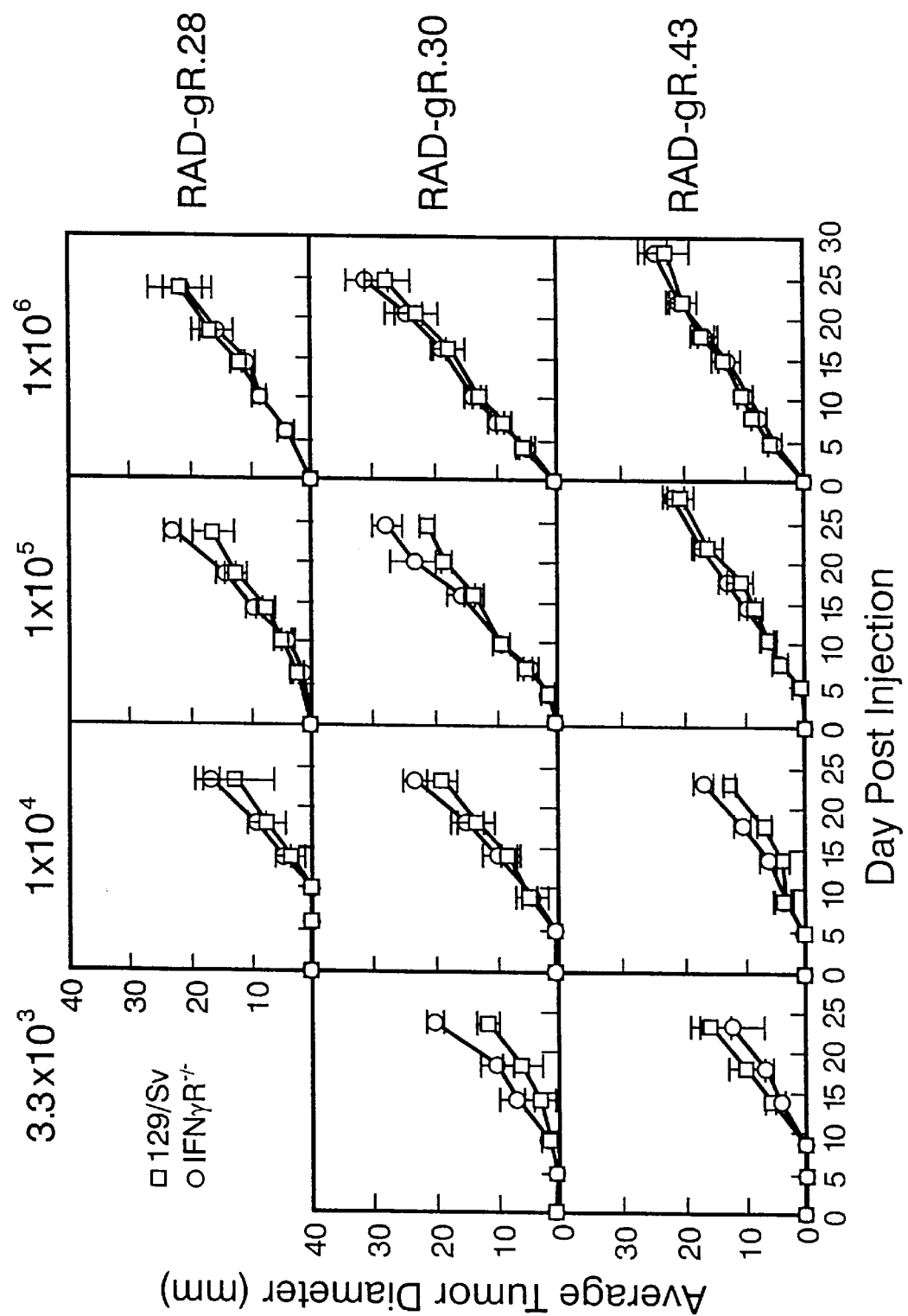
FIG. 2 illustrates the growth of IFNγ-insensitive tumor cells in IFNγ-insensitive and IFNγ-sensitive hosts by plotting as a function of time the average diameter of tumors resulting from subcutaneous injection into naive IFNγR$^{-/-}$ and 129/Sv mice of three representative cell lines derived from IFNγR$^{-/-}$ mice (RAD-gR.28, RAD-gR.30, and RAD-gR.43) at a dose of 3.3×10$^3$, 1×10$^4$, 1×10$^5$, or 1×10$^6$ cells/mouse.

To rule out the possibility that an inoculum of $1 \times 10^6$ RAD-gR cells was sufficiently large to mask minor tumor growth differences in IFNγR−/− and 129/Sv/Ev mice, dose response experiments were performed with three representative RAD-gR cell lines (RAD-gR.28, 30, and 43). Groups of 4–5 naive IFNγR−/− and 129/Sv/Ev mice were injected subcutaneously with $3.3 \times 10^3$ (RAD-gR.30 and 43 only), $1 \times 10^4$, $1 \times 10^5$, or $1 \times 10^6$ cells/mouse. Tumor growth kinetics were monitored by measuring the diameter of the resulting tumor masses and is represented in FIG. 2 as the mean±S.E.M. of 4–5 mice per group.

No differences were detected in the rate of tumor growth kinetics in the IFNγ-sensitive and IFNγ-insensitive mice. Thus, once initiated, IFNγ-insensitive tumors grow progressively in mice regardless of whether IFNγ-responsiveness is present or absent in the host cell compartment.

EXAMPLE 8

This example illustrates that IFNγ-sensitivity of the tumor cell is the critical factor determining tumor growth in vivo.

Figure 3:
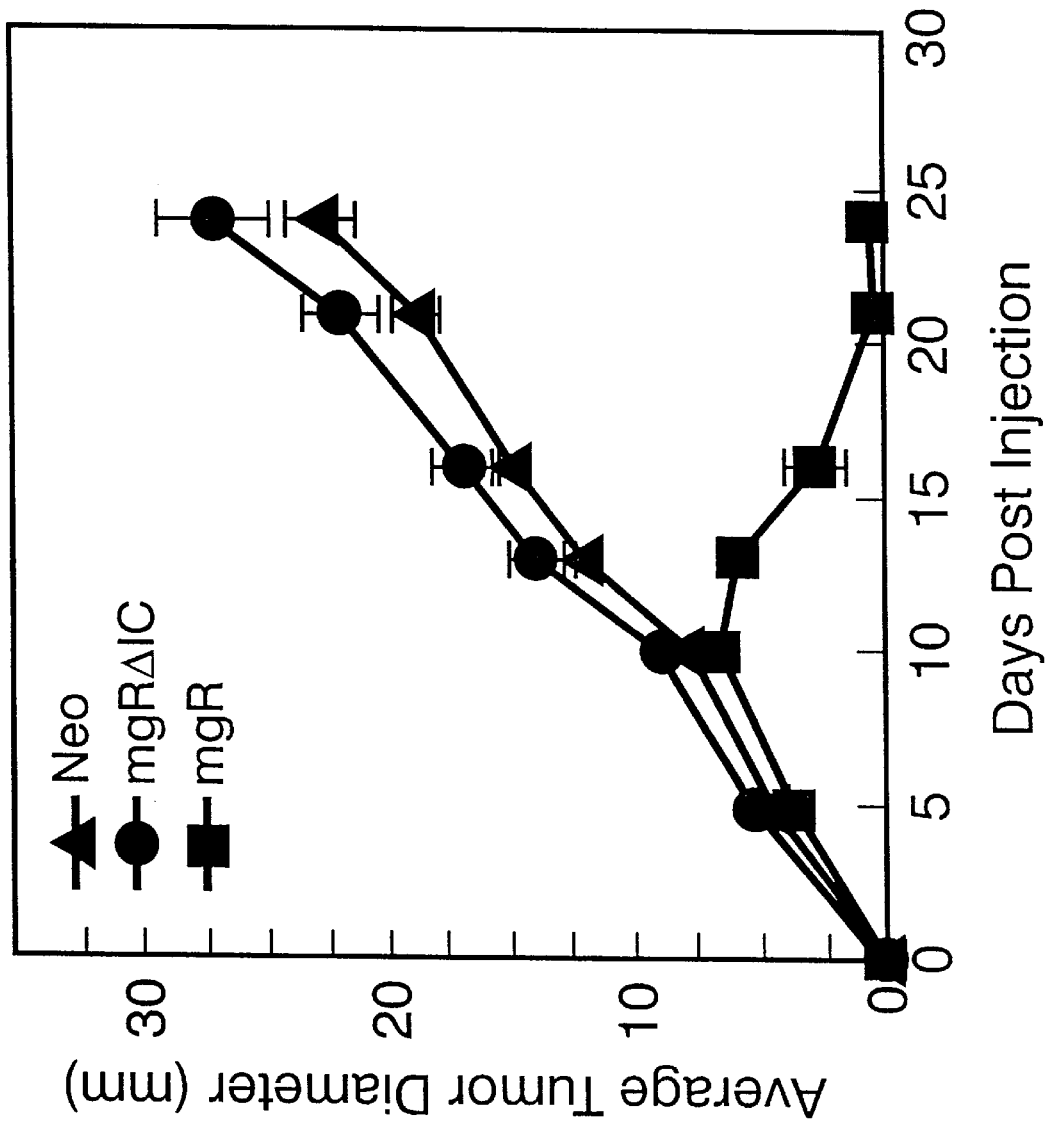
FIG. 3 is a graph showing the average diameter of tumors resulting from subcutaneous injection into naive IFNγ-sensitive 129/Sv mice or IFNγR$^{-/-}$ mice-derived tumor cells transfected with an expression vector encoding the full length IFNγR α chain (mgR), the empty vector (Neo) or a plasmid encoding a functionally inactive IFNγR α chain truncation mutant (mgRΔ/C).

IFNγ responsiveness (as assessed by monitoring IFNγ-dependent cellular expression of MHC class I proteins) was reconstituted in a representative RAD-gR tumor cell line from Example 7. RAD.gR.28 cells were stably transfected with an expression plasmid encoding the full length wild type IFNγR α chain to produce the RAD.gR.28.mgR cell line. Control cell lines were RAD.gR.28 cells transfected with either empty vector (RAD.gR.28.neo) or a plasmid encoding a functionally inactive IFNγR α chain intracellular domain truncation mutant (RAD.gR.28.mgR.ΔIC). Each transfected tumor cell line was then injected subcutaneously at a dose of $10^6$ cells/mouse into groups of 4–5 naive IFNγ-sensitive 129/Sv/Ev mice. Tumor growth kinetics were monitored by measuring the diameter of the resulting tumor masses and the data are shown in FIG. 3, in which tumor growth is represented as the mean ±S.E.M. of each group.

Both of the IFNγ-insensitive tumor cell lines (RAD.gR.28.neo and RAD.gR.28.mgR.ΔIC) formed progressively growing tumors in wild-type mice. In contrast, although the functionally reconstituted RADgR.28.mgR cell line initially produced a small cellular mass in wild-type mice, the mass was eliminated in every animal by day 12 to 15.

In a similar experiment, 129/Sv/Ev mice were injected subcutaneously on day 0 with RAD-gR.28.mgR cells ($10^6$ cells/mouse) and intraperitoneally on days −1, +2, and +5 with 250 μg of a neutralizing monoclonal antibody to IFNγ (H22) (Schreiber et al., J. Immunol. 134:1609, 1985, incorporated herein by reference) or saline. Rejection of the IFNγ-sensitive RAD-gR.28.mgR cells was inhibited in wild type mice treated with the IFNγ-neutralizing antibody.

Taken together, these results show that IFNγ-sensitivity by the tumor is required for the development of an efficient anti-tumor response.

EXAMPLE 9

This example illustrates that IFNγ promotes development of a tumor specific immune response by enhancing immunogenicity of tumor cells.

Having identified the tumor cell as the major target of IFNγ's actions, experiments were designed to define the mechanism underlying the rejection process. IFNγ can induce an antiproliferative state in certain cell types. However, no antiproliferative or anti-metabolic effects of IFNγ either alone or in combination with other cytokines were noted when reconstituted RADgR.28.mgR cells were cultured in the presence of IFNγ in vitro (data not shown).

Figure 4:
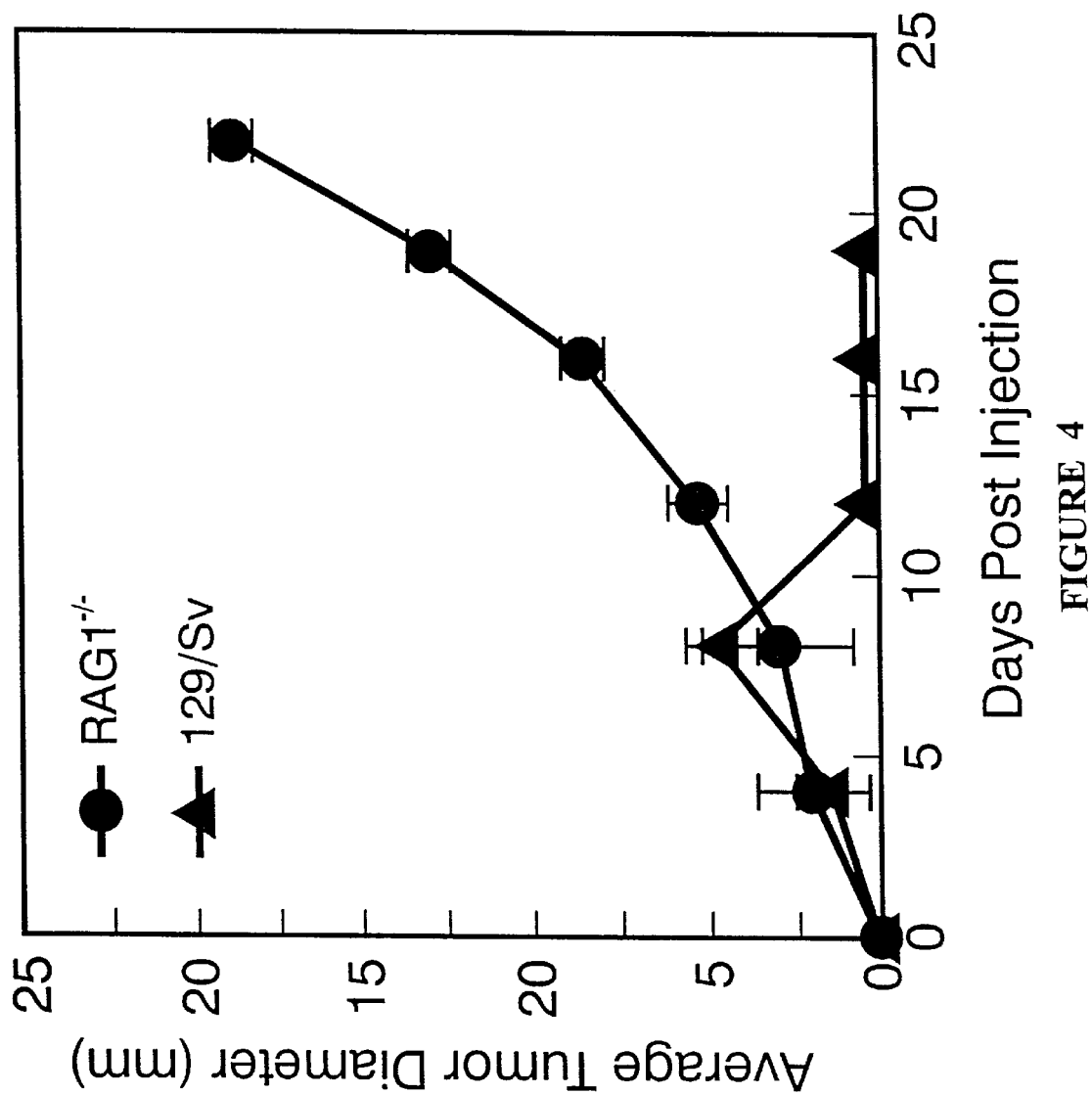
FIG. 4 is a graph illustrating the growth of IFNγ sensitive mgR tumor cells injected subcutaneously into 129/sv wild type and RAG1$^{-/-}$ mice that lack T and B lymphocytes.

The above discussed rejection data could also be explained if IFNγ functioned to enhance tumor cell immunogenicity and thereby promoted development of tumor specific immune responses. To test this hypothesis, the involvement of T cells in rejection of the reconstituted, IFNγ sensitive tumor cell line was investigated using a knockout mouse, RAG1−/−, that lacks T and B lymphocytes (Mombaerts et al., Cell 68:869–77, 1992, which is incorporated by reference). RAD-gR.28.mgR cells were grown in vitro, harvested, and injected subcutaneously at a dose of $10^6$ cells/mouse into groups of 129/Sv/Ev or RAG1−/− mice, with 4 to 5 animals in each group. Tumor kinetics were monitored by measuring the diameter of the resulting tumor masses and the results are represented in FIG. 4 as the means±S.E.M. Whereas IFNγ-sensitive RAD-gR.28.mgR cells were rejected in syngeneic wild type mice, they grew in a progressive manner in the lymphocyte deficient mice.

This experiment was repeated using IFNγ-insensitive RAD-gR.28.neo cells. These IFNγ-insensitive tumor cells grew progressively in both wild type and RAG1−/− mice forming 17 mm tumors after 20 days of in vivo growth (data not shown). Thus, lymphocytes play an obligate role in controlling the growth of reconstituted RAD-gR.28.mgR tumor cells in vivo.

EXAMPLE 10

This example illustrates that a significant number of human tumor cell lines are insensitive to IFNγ.

Considered together, the above data demonstrate that endogenously produced IFNγ forms the basis of a tumor surveillance system in mice that promotes immune recognition and elimination of nascently transformed cells. This concept raises the question of whether naturally occurring tumors can develop a state of IFNγ unresponsiveness in order to escape immune detection and/or elimination.

To address this question IFNγ responsiveness was examined in a variety of tumor cell lines obtained from human tumor cell banks. Established cell lines were cultured in the presence of either buffer, human IFNγ (1000 IRU/ml), or human IFNα$_{A/D}$ (1000 U/ml) for 72 hr followed by quantitation of MHC class I surface expression by flow cytometry with the antibody W6/32 as previously described (Farrar et al., supra). W6/32 is a murine monoclonal antibody specific for a framework region of human MHC Class I and was kindly provided by Dr. Thalachallour Mohanakumar (Washington University, St. Louis, Mo.). IFNγ-dependent STAT1 activation was assessed by treating cells with either PBS or human IFNγ at 10,000 IRU/ml for 5 minutes at 37° C. followed by subjecting 5 μg of nuclear extract to EMSA using a $^{32}$P-labeled GRR probe as described by Greenlund et al., *EMBO J.* 13:1591, 1994, which is incorporated herein by reference.

In a preliminary study of 33 melanoma and 17 lung tumor cell lines classified as non-adenocarcinoma, it was found that approximately 33% of each group showed a quantitative reduction in IFNγ sensitivity (data not shown).

The experiment was repeated with 17 human adenocarcinoma cell lines and the data are shown in Table I below, with the induction of MHC class I expression represented as the mean channel shift between IFNγ-treated cells and untreated cells. Four out of 17 cell lines, SK-LC-2, SK-LC-7, SL-LC-19, and CALU-5, (23.5%) were totally unresponsive to IFNγ either when tested for initiation of IFNγ-signaling or development of an IFNγ dependent biologic response. The CALU-5 cell line was also insensitive to IFNα. None of the cell lines examined show IFNα-specific unresponsiveness. All cell lines were of human origin and displayed aneuploidy. In addition, SK-LC-1, -2, -7, -10, -12, -19 and Calu-5 were tested for expression of the F19 cell surface marker using a rosetting assay and were found to be negative, thereby ruling out the possibility that the cells were of fibroblast origin.

TABLE 1

Analysis of Human Lung Adenocarcinoma Tumors Lines For IFNγ Sensitivity

| Tumor Line | MHC Class I Enhancement (MCS) | | IFNγ Stat Activation | Cellular Defect |
| --- | --- | --- | --- | --- |
| | IFNγ | IFNα | EMSA Analysis | |
| SK-LC-1 | 16.9 | 18.7 | ND | |
| SK-LC-2 | 0.0 | 16.7 | − | Inactive Jak2 |
| SK-LC-4 | 59.5 | 36.7 | + | |
| SK-LC-7 | 0.0 | 37.2 | − | Lacks IFNγR α Chain |
| SK-LC-9 | 49.3 | 53.4 | + | |
| SK-LC-10 | 31.7 | 22.6 | ND | |
| SK-LC-11 | 25.3 | 13.8 | ND | |
| SK-LC-12 | 30.4 | 12.7 | ND | |
| SK-LC-15 | 91.3 | 79.6 | + | |
| SK-LC-16 | 27.0 | 10.9 | + | |
| SK-LC-19 | 0.0 | 25.1 | − | Abnormal Phosphorylated Jak2 |
| SK-LC-20 | 25.6 | 25.9 | + | |
| SK-LU-1 | 47.1 | 16.7 | + | |
| A457 | 27.7 | 27.1 | ND | |
| A549 | 36.9 | 21.8 | ND | |
| CALU-3 | 30.4 | 17.0 | ND | |
| CALU-5 | 0.0 | 0.0 | − | Lacks Jak1 Protein |

To assess whether IFNγ sensitivity could be restored to the four unresponsive cell lines, samples of each line were transfected with expression plasmids encoding one of the IFNγ-signaling proteins using a Biorad Gene Pulser set at 350V and 960 μF. The transfected cell lines were then tested for responsiveness to IFNγ treatment as described above.

Because the CALU-5 cell line could not be successfully transfected, expression of the individual members of the IFNγ-signaling pathway in this cell line was examined by Western blot analysis.

IFNγ sensitivity could be restored in SK-LC-7 by stable transfection with an expression plasmid encoding the IFNγ-receptor a subunit. Similarly, both the SK-LC-2 and SK-LC-19 cell lines became responsive to IFNγ after transfection with expression plasmids encoding Jak2. CALU-5, the only tumor cell line that shows dual insensitivity to IFNγ and IFNα, lacks expression of Jak1, a protein that is required for signaling through both the IFNγ or IFNα receptors, but expresses Jak2, Stat1, and the IFNγ receptor.

These biochemical, immunochemical, and transfection/reconstitution approaches demonstrated that IFNγ unresponsiveness in each cell line is the result of a discrete biochemical lesion which occurs in the family of proteins responsible for the proximal IFNγ-signaling events, i.e. the IFNγ-receptor α and β subunits Jak1, Jak2 and Stat2. Thus, at least certain types of human tumors show a tenency to develop a selective insensitivity to IFNγ, a phenotype that may provide the developing tumor with a growth advantage in vivo.

In summary, it is believed the experiments discussed herein show that IFNγ plays a central role in providing an immunocompetent host with a mechanism of tumor surveillance. This system is operative for both chemically induced and spontaneously arising tumors and thus is likely to represent a generalized mechanism for controlling the development of primary neoplasms in both mice and humans.

Furthermore, the results show that the key target of IFNγ's actions is the transformed cell itself. Based on the extensive amount of information now available concerning IFNγ biology (Bach et al., *Annu. Rev. Immunol.* 15: 563, 1997, incorporated herein by reference), it is most likely that this cytokine is acting to induce formation or presentation of the appropriate antigenic peptide(s) which ultimately leads to immune recognition of the tumor.

This hypothesis predicts that immune recognition of a transformed cell that secondarily acquires a defect in the IFNγ-signaling pathway will be decreased. Thus this cell may go undetected in an immunocompetent host and eventually develop into a progressively growing tumor that may have an extremely aggressive clinical course. It is believed that identification of IFNγ-insensitive tumors may have prognostic and/or therapeutic relevance.

The data also support the concept that IFNγ responsiveness in tumor cells serves a tumor suppressor function. Unlike traditional intrinsic tumor suppressor factors, such as p53, which inhibit transformation, IFNγ works extrinsically together with the adaptive immune response to control the progression of transformed cells into successfully established tumors.

EXAMPLE 11

This example illustrates testing a substance for oncogenicity using IFNγ-insensitive mice.

The substance in a suitable vehicle is injected subcutaneously into a shared region of the back of each member of a test group of 3 6 to 12 week old genetically identical Stat1$^{-/-}$ mice. As a control, the vehicle alone is subcutaneously injected into another group of 3 mice genetically identical Stat1$^{-/-}$ mice of about the same age as in the test groups. Mice in the test and control groups are fed the same diet and kept under the same environmental conditions for a monitoring period of 90 to 180 days. During the monitoring period, the mice are examined every 3–5 days for development of a fibrosarcoma at the injection site.

Alternatively, or in addition, the substance in a suitable vehicle is applied twice weekly on the shaved skin of the back to the test group and the control group is treated with the vehicle alone in the same manner. The test and control groups are examined twice a week over a monitoring period of 90 to 180 days for development of papillomas.

The number and days post-injection of mice with tumors having diameters of over 5 mm is compared in the test and control groups. A higher frequency of tumor formation or earlier tumor onset in the test group than in the control group indicates that the substance is oncogenic.

In view of the above, it will be seen that the several advantages of the invention are achieved and other advantageous results attained.

As various changes could be made in the above methods without departing from the scope of the invention, it is intended that all matter contained in the above description and shown in the accompanying drawings shall be interpreted as illustrative an not in a limiting sense.

What is claimed is:

1. A method for assessing the clinical aggressiveness of a tumor in a patient comprising testing a tumor sample from the patient for sensitivity to interferonγ, the testing comprising (a) treating a sample from the tumor with interferonγ, and
    (b) assaying the treated tumor sample for one or more interferonγ-induced biological effects;
    (c) comparing said one or more interferonγ-induced biological effects on said treated tumor sample to the same one or more interferonγ- induced biological effects on interferonγ sensitive, non-tumor cells taken from said patent as a positive control, wherein induction of one or more interferonγ-induced biological effects in cells of said tumor as compared to non-tumor cells indicates sensitivity to interferonγ, and wherein insensitivity of the tumor to interferonγ is indicative of an aggressive tumor.

2. The method according to claim 1 wherein the patient is a non-human animal.

3. The method according to claim 1 wherein the patient is a human.

4. The method according to claim 1 wherein the one or more interferonγ-induced biological effects comprise enhanced MHC protein expression on the surface of cells of the tumor sample.

5. The method according to claim 4 wherein detection of the enhanced MHC protein expression comprises flow cytometry with an antibody.

6. The method according to claim 5 wherein the antibody is an anti-class-I antibody.

7. The method according to claim 5 wherein the antibody comprises an anti-class II antibody.

8. The method according to claim 1 wherein the one or more interferonγ-induced biological effects comprise the induction of nitric oxide production in tumor cells in the presence of lipopolysaccharide.

9. The method according to claim 1, wherein the one or more interferonγ-induced biological effects comprise the reduction of tumor cell proliferation.

10. The method according to claim 1 wherein the one or more interferonγ-induced biological effects comprise reduction of metabolic activity of the tumor cells.

11. The method according to claim 10, wherein the modulation of metabolic activity of the tumor cells is measured by a thymidine incorporation assay or a 3-[4,5-dimethyl-thiazol-2-yl]2,5-diphenyltetrazolium bromide assay.

12. The method according to claim 1, wherein the one or more interferonγ-induced biological effects comprise a change in the level of mRNA expressed by a gene known to be induced by interferonγ.

13. The method according to claim 12, wherein the gene known to be induced by interferonγ comprises the gene that encodes interferon regulatory factor I (IRF1).

14. The method according to claim 12 wherein the gene known to be induced by interferonγ comprises the gene that encodes guanylate-binding protein (GBP1).

15. The method according to claim 12, wherein the gene known to be induced by interferonγ comprises the gene that encodes MHC class II transactivating protein (CIITA).

16. The method according to claim 12, wherein the gene known to be induced by interferonγ comprises the gene that encodes the complement protein C3.

17. The method according to claim 12, wherein the gene known to be induced by interferonγ comprises the gene that encodes the complement protein factor B.

18. The method of claim claim 1, wherein the non-tumor cells and tumor cells are from the same tissue type.

* * * * *